United States Patent
Raymond et al.

(10) Patent No.: US 12,123,024 B1
(45) Date of Patent: Oct. 22, 2024

(54) ABSOLUTE PRECIPITATION OF EXOSOMES (APEX) ISOLATION

(71) Applicants: Andrea D. Raymond, Coconut Creek, FL (US); Madhavan P. Nair, Coral Gables, FL (US); Arti Vashist, Miami, FL (US); Mickensone Andre, Miami, FL (US)

(72) Inventors: Andrea D. Raymond, Coconut Creek, FL (US); Madhavan P. Nair, Coral Gables, FL (US); Arti Vashist, Miami, FL (US); Mickensone Andre, Miami, FL (US)

(73) Assignee: The Florida International University Board of Trustees, Miami, FL (US)

( * ) Notice: Subject to any disclaimer, the term of this patent is extended or adjusted under 35 U.S.C. 154(b) by 0 days.

(21) Appl. No.: 18/410,576

(22) Filed: Jan. 11, 2024

(51) Int. Cl.
*C12N 5/071* (2010.01)
*C12N 5/00* (2006.01)

(52) U.S. Cl.
CPC .......... *C12N 5/0686* (2013.01); *C12N 5/0081* (2013.01); *C12N 2500/50* (2013.01); *C12N 2501/998* (2013.01)

(58) Field of Classification Search
CPC ........................... C12N 5/0081; C12N 2500/50
See application file for complete search history.

(56) References Cited

PUBLICATIONS

D'souza, 2016, Expert Opinion on Drug Delivery, 13:1257-1275.*
Kontani (1999, Infection and Immunity, 67:4917-4920).*
Pugsley (2007, xPharm: The Comprehensive Pharmacology Reference, pp. 1-7.*
Livshits (2015, Scientific Reports, 5:17319, 14 pages).*
Thery (Current Protocols in Cell Biology (2006) 3.22.1-3.22.29).*
Padin-Gonzalez (2022, Frontiers in Bioengineering and Biotechnology, vol. 10, pp. 1-16.*
Deregibus, Maria Chiara et al. "Charge-based precipitation of extracellular vesicles." International Journal of Molecular Medicine 38, pp. 1359-1366, (Year: 2016).
Jiao, Ruili et al. "A Polyethylene Glycol-Based Method for Enrichment of Extracellular Vesicles from Culture Supernatant of Human Ovarian Cancer Cell Line A2780 and Body Fluids of High-Grade Serous Carcinoma Patients." Cancer Management and Research 12, pp. 6291-6301, (Year: 2020).
Rider, Mark A. "ExtraPEG: A Polyethylene Glycol-Based Method for Enrichment of Extracellular Vesicles." Scientific Reports 6(1): 1-14, (Year: 2016).

* cited by examiner

*Primary Examiner* — Valerie E Bertoglio
(74) *Attorney, Agent, or Firm* — SALIWANCHIK, LLOYD & EISENSCHENK (57) ABSTRACT

The subject invention provides compositions and methods for isolating exosomes from, for example, biological fluid samples, cell cultures and/or cultured medium. Provided are Absolute Precipitation of Exosomes (APEX) reagents and precipitation techniques to isolate exosomes from various EV subsets, cells, dead cells, and/or cell debris. Advantageously, APEX is a rapid, effortless, inexpensive, high-recovery method to extract exosomes. This method is also faster and purer at isolating exosomes from other precipitation techniques.

17 Claims, 8 Drawing Sheets

FIG. 1

APEX Pre-Clear Steps

ABSOLUTE PRECIPITATION OF EXOSOMES (APEX) ISOLATION

BACKGROUND

Cells release extracellular vesicles (EVs) into their environment. EVs can be taken up by a recipient cell to modulate or induce a response. EVs can be grouped based on their sizes such as apoptotic bodies (0.8-5 µm), microvesicles/ectosomes (150 d.nm-1 µm), exosomes (50-150 nm), and exomeres (<50 nm). Unlike liposomes, exosomes are organic lipid bilayer vesicles that are released from most cells when the multivesicular body (MVB) fuses with the plasma membrane. Exosome differs from other EVs by their biogenesis. The surface of exosomes is composed of mostly cholesterols and phospholipids with proteins and glycans on the surface. Inside exosomes are biomolecules such as proteins, RNA, DNA, and lipids. The composition of exosomes tends to resemble the cells that release them.

In addition, many types of organisms from all kingdoms have been found to release exosomes. Exosomes can be found in most biological fluids such as saliva, urine, milk, honey, semen, CSF, and blood plasma. Exosomes are also released into the air like viruses. Exosomes have many physiological functions such as the transportation of biomolecules, cellular communication, and cellular defense. Exosome functions can also be intertwined with pathological processes. For example, cancer cells release abundant exosomes to deactivate the immune cells, induce angiogenesis for cancer progression, and create a niche environment for cancer cells to migrate into during metastasis.

Exosomes are associated with intercellular communication, immune responses, viral pathogenicity, pregnancy, cardiovascular diseases, central nervous system-related diseases, substance use disorders, and cancer progression. Exosomes possess many capabilities from diagnostic to therapeutic applications. Pertaining to oncology, cancer-derived exosomes contain many cancer biomarkers, which is helpful for noninvasive liquor biopsy. Exosomes have also gained attention as nanotherapeutic agents because of their non-immunogenic properties and high drug-loading ability. However, the isolation of exosomes is difficult and expensive.

The gold standard to isolate exosomes is differential centrifugation that culminates in a ultracentrifugation (UC). This method is the purest method to isolate exosomes. The general steps in an ultracentrifugation protocol begin by using submicron filters or low speed centrifugation to remove contaminants such as cell debris, microvesicles, or apoptotic bodies. Subsequently, the exosomes undergo multiple rounds of ultracentrifugation at speeds of 100,000×g or greater to pellet them. Removing the supernatant and then resuspending them in a relatively small volume of buffer produces a concentrated sample useful for investigative purposes. However, such high speeds require not only large initial capital costs but also large maintenance and operating costs. In addition to its high expense, ultracentrifugation is a time-consuming and labor-intensive process typically requiring four to six hours of work by a skilled technician or researcher. It is also necessary to culture high volumes (>100 mL) in order to collect enough exosomes for subsequent experiments. In the end, it still does not produce very pure samples and results in yields of only 5-23%.

Other exosomal isolation methods include differential centrifugation, commercial exosome isolation kits (e.g., ExoQuick-TC™), ultrafiltration, density gradient centrifugation, size exclusion chromatography (SEC), immunoaffinity capture-based isolation, microfluidics-based isolation, and precipitation.

These methods have advantages and disadvantages. For example, the method using the precipitation of exosomes yields a high percentage of exosomes and is capable of handling large sample volumes. This method is one of the best methods to extract RNA from exosomes. However, most precipitation isolation techniques are expensive ($500 per 10 mL) and add unknown elements into the sample. Exo-Quick and Total Exosome Isolation (TEI) are two of the commercial precipitation kits. However, the expense of these kits makes it impossible to perform a large clinical study.

Immunoaffinity capture-based isolation, for example, by magnetic beads and antibody functionalized pillars and packings, works with exosomes with a known antigen. The heterogeneity of exosomes produced by cells limits the efficacy of this approach. Studies have revealed that that there is no commonly agreed upon protein that is abundantly expressed on the surface of exosomes derived from diverse origins. Hence, exosome based-diagnostics that use immunoaffinity capture only succeed in isolating a fraction of the exosomes currently present in a patient. In addition, the isolation process is time-consuming and may require more than a day to achieve optimal recovery rates. Other methods have limitations such as only working with small volumes, requiring large volumes or requiring expensive equipment.

Deregibus et al. (2016) disclose a method based on charge precipitation of EVs from biological fluids and from cell supernatants. However, Deregibus et al. (2016) showed that the total RNA detected in EVs was reduced compared to EVs isolated using differential centrifugation. The APEX procedure does not affect the total RNA content within the isolated EVs. Extracting significant quantities of exosomes from bodily fluids or tissue culture media is difficult due to their small size. Thereby studying exosomes or implementing exosomal research findings in clinical settings is limited. Thus, there is a need for developing methods and reagents for isolating exosomes in sufficient quantities and purities and at reasonable costs of production.

BRIEF DESCRIPTION OF THE INVENTION

The subject invention provides compositions and methods for isolating exosomes and various EV subsets from, for example, solutions, biological fluid samples and/or cultured medium. In one embodiment, the subject invention provides Absolute Precipitation of Exosomes (APEX), an electrostatic charging switching precipitation technique to isolate exosomes and various EV subsets from, for example, cells, dead cells, and/or cell debris, in a biological fluid sample and/or cultured medium. Advantageously, APEX is a rapid, facile, inexpensive, high-recovery method to extract exosomes and various EV subsets. This method is also faster and yields more pure samples of exosomes and various EV subsets compared to other precipitation solutions.

Based on the negative surface charge of exosomes, APEX uses positively charged protein polymers to aggregate exosomes and precipitate them at a lower speed, allowing the differentiation of exosomes from other EV subsets. Advantageously, APEX can yield more exosomes than the UC method and other precipitation methods. Also, APEX is a more affordable method than other commercial exosomal isolation methods.

In one embodiment, the subject invention provides a composition for isolating exosomes from cultural and/or biological samples (e.g., serum and saliva). In certain embodiments, the composition is an APEX solution comprising a positively charged protein, peptide (e.g., protamine), or a salt thereof, and a polymer (e.g., polyethylene glycol (PEG)). In specific embodiments, the APEX solution can be used to isolate exosomes for RNA analysis for all types of diseases and for drug delivery.

EVs have a negative charge that allows the interaction with a positively charged molecule, such as protamine. Advantageously, the positively charged molecule, e.g., protamine can induce EV precipitation from, for example, serum and saliva and from cell culture media without the need for ultracentrifugation. Also, EVs isolated via protamine/PEG precipitation retain biological activity and have no lipoprotein contamination, suggesting the high purity of the obtained EVs.

In specific embodiments, the composition of the subject invention comprises protamine and polyethylene glycol (PEG) at a specific ratio. In a specific embodiment, the APEX solution of the subject invention comprises protamine, polyethylene glycol, and water at certain ratio.

In one embodiment the subject invention provides a method comprising providing a sample (e.g., a biological fluid, cell culture or culture medium); preclearing the sample to remove cells, dead cells, and/or cell debris; mixing the sample with an APEX solution; incubating the mixture of the sample and the APEX solution; and collecting exosomes from the mixture.

In certain embodiments, the sample is a biological fluid selected from, for example, saliva, serum, urine, blood, plasma, tears, sweat, joint fluid, cerebrospinal fluid, semen, vaginal fluid, ascitic fluid, and amniotic fluid.

In certain embodiments, the step of preclearing the sample comprises:
1) centrifuging the sample at about 300×g for at least ten minutes to remove cells from the sample;
2) collecting the supernatant of step 1) and centrifuging the supernatant of step 1) at about 3000×g for at least ten minutes to remove dead cells from the sample;
3) collecting the supernatant of step 2) and centrifuging the supernatant of step 2) at about 20,000×g for at least 30 minutes to remove cell debris from the sample; and
4) collecting the supernatant of step 3).

In specific embodiments, the method of APEX further comprises adjusting the sample to an acidic pH prior to mixing with the APEX solution.

In certain embodiments, the APEX solution comprises a positively charged protein, peptide, or a salt thereof, and a polymer. Preferably, the positively charged protein or peptide is protamine, and the polymer is polyethylene glycol (PEG). In specific embodiments, the APEX solution comprises the positively charged protein, peptide or a salt thereof, and the polymer at a ratio (by weight) of 1:2000, 1:1000, 1:500, 1:400, 1:250, 1:200, 1:100, 1:50, or 1:40.

In specific embodiments, the APEX solution is mixed with the sample at a ratio of 1:1, 1:2, 1:3, 1:4, 1:5, 1:6, 1:7, 1:8, 1:9, or 1:10. In a specific embodiment, the sample is incubated with the APEX solution for at least, 10, 20 or 30 min.

In certain embodiments, the step of collecting exosomes from the mixture comprises centrifuging the mixture, for example, at about 1500 g for at least 30 min; collecting an exosome-containing pellet; and resuspending the exosome-containing pellet.

In one embodiment, the subject invention provides a method for isolating exosomes from a culture medium, the method comprising providing a cell culture; collecting a culture medium of the cell culture; preclearing the culture medium to remove cells, dead cells, and/or cell debris by centrifugation; collecting a supernatant and adjusting the supernatant to a pH from about 4.5 to about 6.5; adding an APEX solution to the supernatant; incubating the mixture of the supernatant and the APEX solution; and isolating exosomes from the mixture.

Advantageously, the method of the subject invention comprises an acidification step, which protects against the loss of total RNA by disrupting RNAses found with the media.

In certain embodiments, preclearing the culture medium comprises:
1) centrifuging the culture medium at about 300×g for at least ten minutes to remove cells;
2) collecting the supernatant of step 1) and centrifuging the supernatant of step 1) at about 3000×g for at least ten minutes to remove dead cells;
3) collecting the supernatant of step 2) and centrifuging the supernatant of step 2) at about 20,000×g for at least 30 minutes to remove cell debris; and
4) collecting the supernatant of step 3).

In a specific embodiment, the APEX solution comprises protamine or a salt thereof, and PEG at a ratio (by weight) of 1:2000, 1:1000, 1:500, 1:400, 1:250, 1:200, 1:100, 1:50, or 1:40.

In specific embodiments, the APEX solution is mixed with the supernatant at a ratio of 1:1, 1:2, 1:3, 1:4, 1:5, 1:6, 1:7, 1:8, 1:9, or 1:10.

In a specific embodiment, the supernatant is incubated with the APEX solution for at least 10, 20, or 30 min.

In certain embodiments, isolating exosomes from the mixture comprises centrifuging the mixture to collect an exosome-containing pellet; and resuspending the pellet in a buffer to arrive at an exosome solution.

DETAILED DESCRIPTION

The subject invention provides compositions and methods for isolating exosomes and various EV subsets from, for example, solutions, biological fluid samples and/or cultured medium. In one embodiment, the subject invention provides Absolute Precipitation of Exosomes (APEX), an electrostatic charging switching precipitation technique to isolate exosomes and various EV subsets from, for example, cells, dead cells, and/or cell debris, in a biological fluid sample and/or cultured medium. Advantageously, APEX is a rapid, facile, inexpensive, high-recovery method to extract exosomes and various EV subsets. This method is also faster and yields more pure samples of exosomes and various EV subsets compared to other precipitation solutions.

Exosomes are small secreted vesicles (typically about 30-150 nm) that may contain, or have present in their membrane, nucleic acid, protein, or other biomolecules and may serve as carriers of cargo between diverse locations in a body or biological system.

In one embodiment, the method of the subject invention is APEX that can precipitate exosomes. Based on the negative surface charge of exosomes, APEX uses positively charged protein polymers to aggregate exosomes and precipitate them at a lower speed, allowing the differentiation of exosomes from other EV subsets. Advantageously, APEX can yield more exosomes than the UC method and other precipitation methods. Also, APEX is a more affordable method than other commercial exosomal isolation methods.

The APEX concept is based on aggregating the exosomes for precipitate at a lower centrifugation speed. Exosomes' negative zeta potential must be neutralized to prevent them from repelling each other. Exosomes tend to have a net negative zeta potential. Thereby positively charged proteins can interact with exosomes to minimize the overall negative charge that exosomes possess and allow the exosomes to aggregate. Proteins can switch their charge from negative to positive based on their isoelectric point and the pH. Lowering the pH causes more proteins to carry a positive charge. Protamine is a positively charged protein with an isoelectric point between 10-13. Accordingly, protamine remains positive at any pH lower than 10. Moreover, at lower pH, more exosomes are isolated because most extracellular proteins in the culture medium carry a positive charge. Ultimately the positively charged proteins help to aggregate and precipitate exosomes. So, this method is inexpensive, less laborious, and can be modified for exosome subset-specific isolations.

To achieve a high concentration of exosomes, the concentration of protamine, the pH of the sample, the ratio of APEX solution to sample, and the incubation time of the APEX solution mixed with the sample can be modified. Results indicate that increasing the protamine concentration, lowering the pH, and increase the ratio of solution to sample significantly increase exosomes yield. The incubating time did not significantly change the exosomes yield but the results indicate the exosomes can be isolate within 30 minutes of incubation time.

In one embodiment, the subject invention provides a composition for isolating exosomes from culture and/or biological samples (e.g., serum and saliva). In certain embodiments, the composition is an APEX solution comprising a positively charged protein or peptide, or a salt thereof (e.g., protamine or protamine chloride), and a polymer (e.g., polyethylene glycol (PEG)). In specific embodiments, the APEX solution can be used to isolate exosomes for RNA analysis for all types of diseases and for drug delivery.

In one embodiment, the subject invention provides an aqueous composition for use in APEX techniques to isolate exosomes and other EV subsets. In one embodiment, the aqueous composition comprises a positively charged protein or peptide or a salt thereof, and a polymer. In a specific embodiment, the positively charged protein is protamine and the polymer is PEG. In some embodiments, PEG has a molar mass ranging from about 300 g/mol to about 10,000,000 g/mol, from about 400 g/mol to about 5,000,000 g/mol, from about 500 g/mol to about 2,000,000 g/mol, from about 600 g/mol to about 1,000,000 g/mol, from about 700 g/mol to about 500,000 g/mol, from about 800 g/mol to about 200,000 g/mol, from about 900 g/mol to about 100,000 g/mol, from about 1000 g/mol to about 100,000 g/mol, from about 2000 g/mol to about 100,000 g/mol, from about 3000 g/mol to about 90,000 g/mol, from about 4000 g/mol to about 80,000 g/mol, from about 5000 g/mol to about 70,000 g/mol, from about 6000 g/mol to about 60,000 g/mol, from about 7000 g/mol to about 50,000 g/mol, from about 8000 g/mol to about 40,000 g/mol, from about 9000 g/mol to about 30,000 g/mol, or from about 10,000 g/mol to about 20,000 g/mol. In a specific embodiment, PEG is PEG 35,000.

In certain embodiments, the aqueous composition of the subject invention has a pH from about 3 to about 12, from about 3.5 to about 11, from about 4 to about 10, from about 4.5 to about 9, from about 5 to about 9, from about 5.5 to about 8.5, from about 6 to about 8.5, from about 6.5 to about 8, from about 5 to about 7.5, from about 5.5 to about 7.5, from about 5 to about 7, from about 5 to about 6.5, from about 5.5 to about 7, from about 4.5 to about 7, from about 3.5 to about 6.5, from about 4.5 to about 6.5, from about 3.5 to about 6, or from about 3.5 to about 5.5.

In certain embodiments, the aqueous composition of the subject invention has a pH of 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, or 7.5.

In certain embodiments, the composition comprises the positively charged protein/peptide or salt thereof, and polymer at a ratio (by weight) between 1:5000 and 1:10, between 1:4000 and 1:10, between 1:3000 and 1:10, between 1:2000 and 1:10, between 1:1500 and 1:10, between 1:1000 and 1:10, between 1:900 and 1:20, between 1:800 and 1:30, between 1:700 and 1:40, between 1:600 and 1:50, between 1:500 and 1:50, between 1:400 and 1:50, between 1:300 and 1:60, between 1:200 and 1:70, between 1:100 and 1:80, between 1:100 and 1:10, between 1:200 and 1:10, between 1:300 and 1:10, or between 1:400 and 1:10. In specific embodiments, the composition comprises the positively charged protein/peptide and polymer at a ratio (by weight) of 1:2000, 1:1000, 1:500, 1:400, 1:250, 1:200, 1:100, 1:50, or 1:40.

In certain embodiments, the composition comprises protamine and PEG at a ratio (by weight) between 1:5000 and 1:10, between 1:4000 and 1:10, between 1:3000 and 1:10, between 1:2000 and 1:10, between 1:1500 and 1:10, between 1:1000 and 1:10, between 1:900 and 1:20, between 1:800 and 1:30, between 1:700 and 1:40, between 1:600 and 1:50, between 1:500 and 1:50, between 1:400 and 1:50, between 1:300 and 1:60, between 1:200 and 1:70, between 1:100 and 1:80, between 1:100 and 1:10, between 1:200 and 1:10, between 1:300 and 1:10, or between 1:400 and 1:10. In specific embodiments, the composition comprises protamine and PEG at a ratio (by weight) of 1:2000, 1:1000, 1:500, 1:400, 1:250, 1:200, 1:100, 1:50, or 1:40.

In certain embodiments, the composition comprises, consists essentially of, or consists of a positively charged protein/peptide or a salt thereof, a polymer and water at a ratio (by weight) of 1:2000:10,000, 1:1000:5000, 1:400:2000, 1:200:1000, 1:100:500, 1:50:250, 1:40:200, 1:20:100, or any ratio range in between.

In one embodiment, the subject invention provides a method of Absolute Precipitation of Exosomes (APEX) from a sample, the method comprising:
  preclearing the sample to remove cells, dead cells, and/or cell debris (e.g., other organelles and microvesicles) from the sample;
  mixing the sample with an APEX solution;
  incubating the mixture of the sample and the APEX solution; and
  collecting exosomes from the mixture of the sample and the APEX solution.

In one embodiment, the sample can be selected from, for example, a biological fluid, conditioned media, cell media, and culture medium. The term biological fluid, as used herein, means any fluid isolated or derived from an organism including prokaryotes, eukaryotes, bacteria, fungi, yeast, invertebrates, vertebrates, reptiles, fish, insects, plants and animals.

In specific embodiments, the biological fluid is selected from, for example, saliva, serum, urine, blood, plasma, tears, sweat, joint fluid, cerebrospinal fluid, semen, vaginal fluid, ascitic fluid, and amniotic fluid. In some embodiments, the biological fluid sample may be obtained from a subject such as mouse, rat, guinea pig, rabbit, dog, cat, bovine, horse, goat, sheep, primate or human.

In some embodiments, exosomes may also be isolated from tissue samples such as surgical samples, biopsy samples, tissues, feces, plant tissue, insect tissue, and cultured cells. When isolating exosomes from tissue sources it may be necessary to homogenize the tissue in order to obtain a single cell suspension followed by lysis of the cells to release the exosomes. When isolating exosomes from tissue samples it is important to select homoginazation and lysis procedures that do not result in disruption of the exosomes. Exosomes may be isolated from freshly collected samples or from samples that have been stored frozen or refrigerated.

In certain embodiments, the step of preclearing the sample comprises:
  1) centrifuging the sample (e.g., at about 300×g for ten minutes or longer) to pellet cells, if any, in the sample;
  2) collecting the supernatant of step 1) and centrifuging the supernatant of step 1) (e.g., at about 3000×g for ten minutes or longer) to pellet dead cells, if any, in the sample;
  3) collecting the supernatant of step 2) and centrifuging the supernatant of step 2) (e.g., at about 20,000×g for 10, 20, 30 minutes or longer) to pellet cells debris such as organelles and microvesicles, if any, in the sample; and
  4) collecting the supernatant of step 3).

In certain embodiments, the supernatant collected at the end of the preclearing step is adjusted to a proper pH by using either an acid or a base. In a specific embodiment, the acid is HCl, $HNO_3$, or $H_2SO_4$. In a specific embodiment, the base is NaOH or KOH. In specific embodiments, the method further comprises adjusting the sample to an acidic pH prior to mixing with the APEX solution.

In certain embodiments, the pH of the supernatant collected at the end of the preclearing step is adjusted to a pH from about 3 to about 12, from about 3.5 to about 11, from about 4 to about 10, from about 4.5 to about 9, from about 5 to about 9, from about 5.5 to about 8.5, from about 6 to about 8.5, from about 6.5 to about 8, from about 5 to about 7.5, from about 5.5 to about 7.5, from about 5 to about 7, from about 5 to about 6.5, from about 5.5 to about 7, from about 4.5 to about 7, from about 3.5 to about 6.5, from about 4.5 to about 6.5, from about 3.5 to about 6, or from about 3.5 to about 5.5.

In certain embodiments, the pH of the supernatant collected at the end of the preclearing step is adjusted to 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, or 8.5.

In preferred embodiments, the pH of the supernatant collected at the end of the preclearing step is adjusted to an acidic pH from about 3 to about 7, from about 3.5 to about 7, from about 4 to about 7, from about 4.5 to about 7, from about 5 to about 7, from about 5.5 to about 7, from about 3 to about 6.5, from about 3.5 to about 6.5, from about 4 to about 6.5, from about 4.5 to about 6.5, from about 5 to about 6.5, from about 5.5 to about 6.5, from about 3.5 to about 6, from about 3.5 to about 5.5, from about 4 to about 6, from about 4 to about 5.5, or from about 3.5 to about 5.

In certain embodiments, the method comprises adding the APEX solution to the acidic sample, wherein the APEX solution is added at an APEX to sample ratio of 1:1, 1:2, 1:3, 1:4, 1:5, 1:6, 1:7, 1:8, 1:9, or 1:10.

In certain embodiments, the sample is mixed and incubated with the APEX solution for at least 10 min, 20 min, 30 min, 40 min, 50 min, 60 min, 70 min, 80 min, 90 min, 100 min, 110 min, 120 min, 3 hours, 4 hours, 5 hours, 6 hours, 7 hours, 8 hours, 9 hours, 10 hours or 12 hours. In certain embodiments, the sample is mixed and incubated with the APEX solution for about 10 min to about 24 hours, about 30 min to about 20 hours, about 30 min to about 18 hours, about 30 min to about 16 hours, about 30 min to about 12 hours, about 30 min to about 10 hours, or about 30 min to about 8 hours.

In specific embodiments, incubation of the sample with the APEX solution may be performed at a reduced temperature such as 4° C. In some embodiments, incubation may be performed at 1° C. to 40° C., 1° C. to 4° C., 4° C. to 10° C., 10° C. to 20° C., or 20° C. to 30° C.

In one embodiment, the step of collecting exosomes from the mixture of the sample and the APEX solution comprises centrifuging the mixture at about 1,500 g for at least 10, 20, 30 min; collecting an exosome-containing pellet; and resuspending the pellet in a proper solution or buffer (e.g., PBS or saline) to arrive at an exosome solution.

In some embodiments, other buffers commonly used for biological samples may be used for the exosomes, including phosphate, acetate, citrate and TRIS buffers. The pH of the buffer may be any pH that is compatible with the sample, but a typical range is from 6 to 8. The buffer may have a pH from 4 to 10, 4 to 6, 4 to 8, 6 to 10, 6 to 8, or 8 to 10. The salt concentration can be any concentration that is compatible with the sample, but typically ranges from about 10 mM to about 500 mM. The salt concentration may be about 10 mM to about 500 mM, about 10 mM to about 50 mM, about 10 mM to about 100 mM, about 10 mM to about 200 mM, about 10 mM to about 300 mM, about 10 mM to about 400 mM, about 50 mM to about 500 mM, about 100 mM to about 500 mM, about 200 mM to about 500 mM, about 300 mM to about 500 mM, or about 400 mM to about 500 mM.

In one embodiment, the subject invention provides a method for isolating exosomes from a sample, the method comprising:
1) centrifuging the sample (e.g., at about 300×g for ten minutes or longer,) to remove cells from the sample;
2) collecting the supernatant of step 1) and centrifuging the supernatant of step 1) (e.g., at about 3000×g for ten minutes or longer) to remove dead cells from the sample;
3) collecting the supernatant of step 2) and centrifuging the supernatant of step 2) (e.g., at about 20,000×g for 10, 20, 30 minutes or longer) to remove cells debris such as organelles and microvesicles from the sample;
4) collecting the supernatant of step 3);
5) mixing the supernatant of step 3) with an APEX solution;
6) incubating the mixture of step 5);
7) centrifuging the mixture (e.g., at about 1,500 g for at least 10, 20, 30 min) to collect an exosome-containing pellet; and resuspending the pellet in a buffer (e.g., PBS or saline) to arrive at an exosome solution.

In specific embodiments, the method for isolating exosomes from a sample further comprises adjusting the supernatant of step 3) to an acidic pH, for example, between 3.5 and 6.5.

In one embodiment, the method of the subject invention provides an exosome recovery rate of at least 20%, 25%, 30%, 35%, 40%, 45%, 50%, 55%, 60%, 65%, 70%, 75%, 80%, 85%, 90%, or 95%.

In one embodiment, the subject invention provides a method for isolating exosomes from other EV subsets from a sample, the method comprising preclearing the sample to remove cells, dead cells, and/or cell debris (e.g., other organelles and microvesicles) from the sample; mixing the sample with an APEX solution; incubating the mixture of the sample and the APEX solution; and collecting exosomes from the mixture of the sample and the APEX solution. In specific embodiments, the method may further comprise adjusting the sample to an acidic pH prior to mixing the sample with the APEX solution.

In one embodiment, the subject invention provides a method for isolating exosomes from other EV subsets from a culture medium, the method comprising preclearing the culture medium to remove cells, dead cells, and/or cell debris (e.g., other organelles and microvesicles) by centrifugation; collecting the supernatant after the centrifugation; adding an APEX solution to the supernatant; incubating the mixture of the supernatant and the APEX solution; and collecting exosomes from the mixture. In specific embodiments, the method may further comprise adjusting the supernatant to an acidic pH prior to mixing with the APEX solution.

In one embodiment, the subject invention provides a method for isolating exosomes from a culture medium, the method comprising providing a cell culture; collecting the culture medium; preclearing the culture medium to remove cells, dead cells, and/or cell debris by centrifugation; collecting a supernatant; adding an APEX solution to the supernatant; incubating the mixture of the supernatant and the APEX solution; and isolating exosomes from the mixture. In specific embodiments, the method further comprises adjusting the supernatant to an acidic pH prior to mixing with the APEX solution.

In one embodiment, preclearing the culture medium comprises:
1) centrifuging the culture medium at about 300×g for at least ten minutes to remove cells from the culture medium;
2) collecting the supernatant of step 1) and centrifuging the supernatant of step 1) at about 3000×g for at least ten minutes to remove dead cells;
3) collecting the supernatant of step 2) and centrifuging the supernatant of step 2) at about 20,000×g for at least 10, 20 or 30 minutes to remove organelles and microvesicles; and
4) collecting the supernatant of step 3).

In one embodiment, the step of isolating exosomes from the mixture of the supernatant and the APEX solution comprises centrifuging the mixture to collect an exosome-containing pellet; and resuspending the pellet in a buffer (e.g., PBS or saline) to arrive at an exosome solution.

In one embodiment, the subject invention provides a method for isolating exosomes from other EV subsets from a culture medium, the method comprising:
1) centrifuging the culture medium (e.g., at about 300×g for ten minutes or longer,) to remove cells;
2) collecting the supernatant of step 1) and centrifuging the supernatant of step 1) (e.g., at about 3000×g for ten minutes or longer) to remove dead cells;
3) collecting the supernatant of step 2) and centrifuging the supernatant of step 2) (e.g., at about 20,000×g for 10, 20, 30 minutes or longer) to remove cells debris such as organelles and microvesicles;
4) collecting the supernatant of step 3);
5) mixing the supernatant of step 3) with an APEX solution;
6) incubating the mixture of step 5);
7) centrifuging the mixture (e.g., at about 1,500 g for at least 10, 20, 30 min) to collect an exosome-containing pellet; and resuspending the pellet in a buffer (e.g., PBS or saline) to arrive at an exosome solution.

In specific embodiments, the method further comprises adjusting the supernatant of step 3) to an acidic pH, for example, between 3.5 and 6.5.

In certain embodiments, the subject invention provides a method for isolating microvesicles from a sample, the method comprising
1) centrifuging the sample (e.g., at about 300×g for ten minutes or longer,) to remove cells from the sample;
2) collecting the supernatant of step 1) and centrifuging the supernatant of step 1) (e.g., at about 3000×g for ten minutes or longer) to remove dead cells from the sample;

3) collecting the supernatant of step 2) and centrifuging the supernatant of step 2) (e.g., at about 20,000×g for 10, 20, 30 minutes or longer) to collect a microvesicle-containing pellet;
4) resuspending the microvesicle-containing pellet in a buffer; and
5) isolating microvesicles from the buffer.

In one embodiment, the subject invention provides a method for producing a pure exosome solution, the method comprising:
providing a cell culture, wherein the cells secret exosomes into the culture medium;
collecting the culture medium;
preclearing the culture medium to remove cells, dead cells, and/or cell debris (e.g., other organelles and microvesicles) by centrifugation;
collecting the supernatant;
adding an APEX solution to the supernatant;
incubating the mixture of the supernatant and the APEX solution; and
collecting exosomes from the mixture by centrifuging the mixture (e.g., at about 1,500 g for at least 10, 20, 30 min) to collect an exosome-containing pellet; and resuspending the pellet in a buffer, e.g., PBS or saline, to arrive at an exosome solution.

In specific embodiments, the method further comprises adjusting the supernatant to an acidic pH prior to adding the APEX solution.

In some embodiments, the cell culture is a primary cell culture or a cultured cell line. In some embodiments, the cells may be isolated or derived from an organism including prokaryotes, eukaryotes, bacteria, fungi, yeast, invertebrates, vertebrates, reptiles, fish, insects, plants and animals. In specific embodiments, the cells may be obtained from a subject such as mouse, rat, guinea pig, rabbit, dog, cat, bovine, horse, goat, sheep, primate or human.

In specific embodiments, the cells can be stem cells such as bone marrow stem cells (BMSCs). Preferably, the BMSCs are bone marrow mesenchymal stem cells (MSCs). The term "mesenchymal stem cell" or "MSC", as used herein, refers to a multipotent somatic stem cell derived from mesoderm, having self-regenerating and differentiating capacity to produce progeny cells with a large phenotypic variety, including connective tissues, stroma of bone marrow, adipocytes, dermis and muscle, among others. MSCs may be isolated from any type of tissue. Generally, MSCs may be isolated from bone marrow, adipose tissue, umbilical cord, or peripheral blood. In a particular embodiment, the MSCs are bone marrow-derived stem cells.

"Bone marrow mesenchymal stem cells," or "bone marrow derived mesenchymal stem cells" refer to cells existing in the bone marrow, which can be directly collected from the bone marrow or indirectly collected from other tissues (e.g., blood, skin, fat, and other tissues), and can be cultured and proliferated as adherent cells on a solid surface, e.g., a culture dish (made of plastic or glass). These cells are characterized in having a potential to differentiate into mesenchymal tissues such as bone, cartilage, and fat, or into skeletal muscle, heart muscle, nervous tissues, and epithelial tissues, and can be obtained by collection of bone marrow cells. Markers for human bone marrow mesenchymal stem cells can be, for example, all or some of the following, but are not limited to, Lin-negative, CD45-negative, CD44-positive, CD90-positive, and CD29-positive.

In some embodiments, the stem cells are cancer stem cells (CSCs). Eight sub-types of CSCs have been identified with varying potential for use as regenerative therapy agents:

1) Cardiosphere-Derived Cells (CDCs); clusters of cardiac progenitor, endothelial and mesenchymal cells which have shown improvement in ventricular ejection fraction and reduction in heart failure status.
2) Sca-1+ CSCs; reside in various regions of the human heart and although they have been shown to be capable of differentiating into cardiomyoblasts, no clinical trials have been conducted with this cell type.
3) Cardiac Mesoangioblasts; shown to exhibit differentiation into cardiomyocytes in vitro, transplanted cells however showed limited proliferation, migration or paracrine activity.
4) Cardiac Side Population cells; possess stem cell-like properties but their ability to differentiate into cardiomyocites is under debate and they are depleted with advancing age. They are considered unlikely candidates for clinical studies.
5) Islet-1+ CSCs; cells committed towards the cardiomyocyte lineage with differentiation capability towards all three cardiovascular lineages, their scarcity in the human heart limits their use in cell replacement therapy.
6) Epicardium-Derived Progenitor cells; quiescent epicardial cells have been shown to undergo epithelial-to-mesenchymal transition post infarct and to migrate into the infarcted myocardium to participate in cardiac repair.
7) Cardiac Colony-Forming-Unit Fibroblasts; exhibit MSC properties with proliferation and differentiation capacities into endothelial and smooth muscle cells, but not into cardiomyocytes, suggesting limited potential for regenerating cardiac muscle.
8) W8B2+ CSCs; reside in human atrial appendages and can differentiate into cardiovascular lineages, showed low engraftment but powerful paracrine effects with promising potential for cardiac therapy and regeneration.

In one embodiment, the method of the subject invention further comprises measuring the size distribution of the collected exosomes for confirmation; measuring the concentration of exosomes in the exosome solution; measuring the total protein content in exosomes and/or detecting one or more specific proteins or factors in exosomes.

Exosomes may contain, for example, cytokines and growth factors, lipids, mRNAs, and regulatory miRNAs. Exosomes may contain a conserved set of proteins including tetraspanins (e.g., CD81, CD63, and CD9), heat-shock proteins (e.g., HSP60, HSP70 and HSP90), targeting or adhesion markers such as integrins, ICAM-1, EpCAM, membrane fusion markers such as annexins, tumor susceptibility gene 101 (TSG101), and/or ALIX; and may also contain unique tissue-specific proteins that reflect their cellular origins, for example, cardiac tissue-specific proteins such as serum albumin, serotransferrin, and alpha-2-macroglobulin. Exosomes may further comprise vascular endothelial growth factor (VEGF), interleukin-6 (IL-6), IL-10, transforming growth factor beta 1 (TGF-β1), fibroblast growth factor 2 (FGF-2), extracellular matrix metalloproteinase inducer (EMMPRIN), MMP-9, hepatocyte growth factor (HGF) and granulocyte colony stimulating factor (G-CSF).

In some embodiments, the exosome solution comprises at least $1 \times 10^n$ exosomes (n≥5)/µl. In certain embodiments, the exosome solution comprises about $1 \times 10^5$/µl to about $1 \times 10^{15}$/µl, about $1 \times 10^6$/µl to about $1 \times 10^{14}$/µl, about $1 \times 10^7$/µl to about $1 \times 10^{13}$/µl, about $1 \times 10^8$/µl to about $1 \times 10^{12}$/µl, about $1 \times 10^8$/µl to about $1 \times 10^{11}$/µl, about $1 \times 10^8$/µl to about $1 \times 10^{10}$/µl, or about $1 \times 10^8$/µl to about $1 \times 10^9$/µl exosomes.

In one embodiment, the method may further comprise analyzing isolated exosomes using any method that allows direct or indirect visualization of exosomes and may be in vivo or ex vivo. For example, analysis may include, but not limited to, ex vivo microscopic or cytometric detection and visualization of exosomes bound to a solid substrate, flow cytometry, fluorescent imaging, and the like. The exosomes may be analyzed by flow cytometric expression of the exosome surfaces markers, and/or transmission electron microscopy (TEM).

In certain embodiments, the subject invention provides kits that comprise one or more vessels containing the positively charged protein/peptide and/or the polymer, one or more buffers or one more solutions for performing centrifugations of exosomes.

In some embodiments, the exosomes collected via the methods of the subject invention may be used for restoring heart function, regenerating heart tissue, and/or treating degenerative diseases. In some embodiments, the exosomes may be formulated in any forms that are suitable for local, oral, parenteral (e.g., intravenous, intraarterial, intraperitoneal, intrathecal, intraventricular, intradermal, intracavity, subcutaneous or intramuscular) administration, including solutions, suspensions, liposomes, microspheres, and nanosystems suitable for solutions or suspensions in liquid prior to injection.

In one embodiment, the degenerative disease is selected from: cardiovascular disease, arthritis, Friedreich ataxia, Huntington's disease, Kennedy's disease, Marfan syndrome, multiple sclerosis, motor neurone disease (MND), muscular dystrophy, myasthenia gravis, Parkinson's disease, and Alzheimer's disease.

As used herein, the singular forms "a," "an," and "the" are intended to include the plural forms as well, unless the context clearly indicates otherwise. Furthermore, to the extent that the terms "including," "includes," "having," "has," "with," or variants thereof are used in either the detailed description and/or the claims, such terms are intended to be inclusive in a manner similar to the term "comprising." The transitional terms/phrases (and any grammatical variations thereof) "comprising," "comprises," and "comprise" can be used interchangeably; "consisting essentially of," and "consists essentially of" can be used interchangeably; and "consisting," and "consists" can be used interchangeably.

The transitional term "comprising," "comprises," or "comprise" is inclusive or open-ended and does not exclude additional, unrecited elements or method steps. By contrast, the transitional phrase "consisting of" excludes any element, step, or ingredient not specified in the claim. The phrases "consisting" or "consists essentially of" indicate that the claim encompasses embodiments containing the specified materials or steps and those that do not materially affect the basic and novel characteristic(s) of the claim. Use of the term "comprising" contemplates other embodiments that "consist" or "consisting essentially of" the recited component(s).

When ranges are used herein, such as for dose ranges, combinations and subcombinations of ranges (e.g., subranges within the disclosed range), specific embodiments therein are intended to be explicitly included.

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 0-20%, 0 to 10%, 0 to 5%, or up to 1% of a given value. Where particular values are described in the application and claims, unless otherwise stated the term "about" meaning within an acceptable error range for the particular value should be assumed. In the context of compositions containing amounts of concentrations of ingredients where the term "about" is used, these values include a variation (error range) of 0-10% around the value (X±10%).

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. It will be further understood that terms, such as those defined in commonly used dictionaries, should be interpreted as having a meaning that is consistent with their meaning in the context of the relevant art and/or as otherwise defined herein.

EXAMPLES

Materials and Methods

Cell Culture

HEK293T cells were cultured in DMEM media (Gibco) supplemented with 10% FBS (Gibco) and 1% Pen at 37° C., 5% CO2.

Absolute Precipitation of Exosomes (APEX) Preparation

Figure 1:
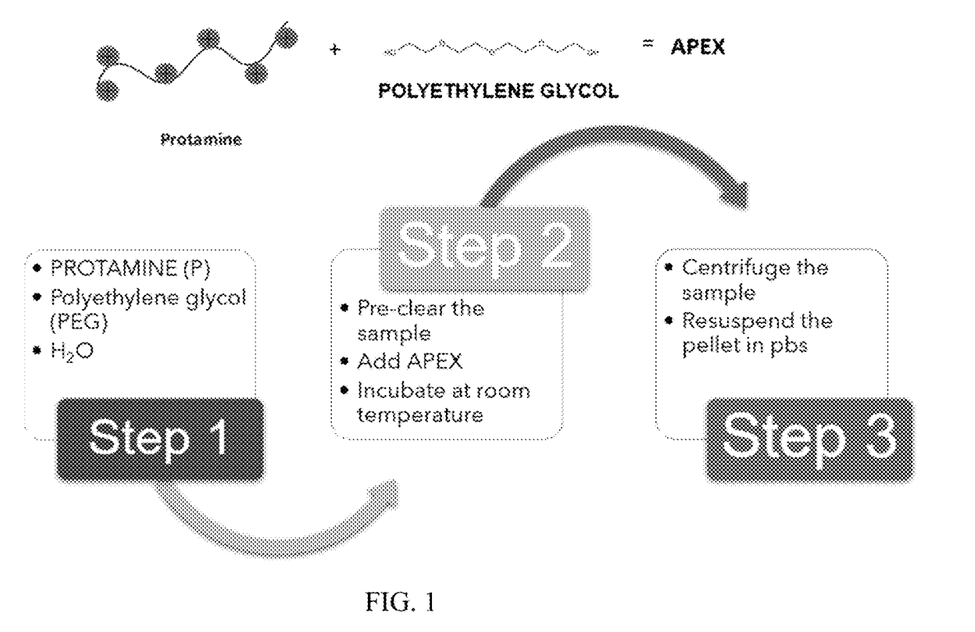
FIG. 1 shows a protocol of Absolute Precipitation of Exosomes (APEX).
Figure 2A:
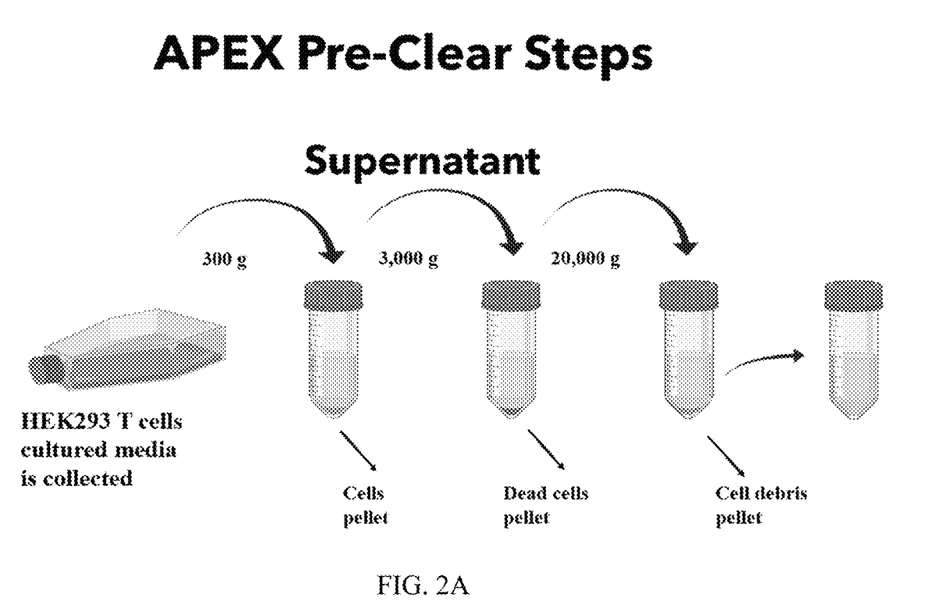
FIGS. 2A-2B show APEX isolation of exosomes. (2A) APEX pre-clear steps, and (2B) APEX experimental procedure.

APEX is composed of Poly(ethylene glycol) PEG 32,000, protamine chloride, and water (FIG. 1). The concentration of PEG 32,000 was kept at 0.200 g per mL of water. The concentration of Protamine chloride varies (4, 2, 1, and 0.5 mg/mL). HEK293T cells were seeded at 1E6 into three T-75 flasks and grown for 3-4 days. The cultured media was collected at confluency, pooled, and then precleared at 300×g for ten minutes. The supernatant was collected and centrifuged at 3000×g for ten minutes. The pellet was discarded, and the supernatant centrifuged at 20,000×g for 30 minutes, to remove cells, dead cells, and cell debris such as organelles and microvesicles, respectively (FIG. 2A).

Figure 2B:
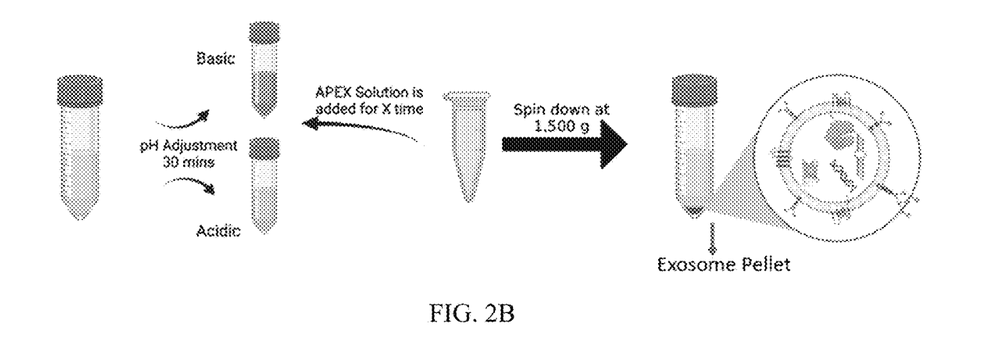

Next, the pH of the sample was adjusted with 1M HCl or 1M NaOH for 30 mins at 4° C. Afterward, the APEX solution was added to the samples at different ratios. Samples were then incubated with APEX at a time point and finally centrifuged at 1,500 g for 30 mins. The pellet was resuspended in 200 uL of PBS for later analysis (FIG. 2B).

Different formulation ratios of Protamine: PEG (0.5:200, 1:200, 2:200, 4:200) mg, APEX to sample ratio (1:3, 1:4, 1:5), the pH (5.5, 6.5, 7.4, 8.5), and incubated time point at 4° C. (30 min, 1 hour, 2 hours, 4 hours, 8 hours and overnight) were tested and compared.

For the UC method, cultured media was precleared by centrifuging the sample at 300 g, 3000 g, and 20,000 g and collecting the supernatant each time. Finally, the sample was centrifuged at 120,000 g for 70 minutes to pellet down the exosomes. The exosomal pellet was washed with 1 mL of PBS and centrifuged at 120,000 g for 70 minutes. The exosomes pellet was resuspended in 200 μL of PBS.

For the Exoquick exosome isolation method, the sample was precleared with 2000 g for 10 minutes twice. Exoquick was then added to the sample at a ratio of 1:5 and incubated overnight, followed by a 1,500 g centrifuge for 30 mins. The pellet was resuspended in 200 μl of PBS.

Total Protein Assay

To measure the total protein, the sample was lysed in RIPA buffer containing protease inhibitors at a ratio of 1:1 and then the samples were centrifuged at 14,000 g for 15 mins. The supernatant was collected for further analysis. Protein concentration was quantified by Bio-Rad DC Protein Assay kit.

Western Blot

Samples were loaded based on equal protein (15 µg) or volume (3-15 µL). Samples were loaded into an SDS-PAGE gel and transferred to a PVDF membrane. The membrane was blocked with 2% milk in TBST buffer. Primary antibodies were rabbit Anti-ALIX (1:2800), rabbit Anti-CD63 (1:2800), rabbit Anti-HSP70 (1:2800), and rabbit Anti-TSG101 (1:2800) in TBST with 1% milk. Horseradish peroxidase (HRP)-conjugated secondary antibody (1:100,000) in TBST with 2% milk. Femto chemiluminescence was used for detection.

Zetasizer and Zeta Potential

Dynamic Light Scattering (DLS) was used to measure the hydrodynamic size of APEX precipitation (Malvern Instruments, UK). Samples were diluted 10:1000 in PBS.

Vesicle Quantification Using Fluorocet and RFP Fluorescence

HEK 293T cells were transfected with an Xpack plasmid to express RFP exosomes. The culture medium was collected and pooled together. All 14 APEX parameters, UC, and Exo-Quick were implemented. The pellet was resuspended in 200 µL of PBS. 239T RFP Xpack exosomes (Rex) were quantified by adding equal volume of the exosomes resuspended in PBS into each well and analyze the fluorescence intensity via a Fluorometer (520 ex, 560 em). The samples were diluted and placed in their respective wells in a 96-well plate synergy LX multi-mode reader BioTek.

Nanoparticle Tracking Analysis (NTA)

The NanoSight LM10 was set to capture 5 frames (30 s each) for each sample with background level at 10, camera level at 12 and shutter speed at 30. Captured nanoparticles in 3D distribution images were analyzed using NTA software (Version 3.2 Build 16). The exosomes samples were diluted 10:1000 in PBS and filtered through 0.2 µm filter. PBS was used to wash the instrument after each run. Three videos of 30 seconds were recorded of each exosome sample.

Statistical Analyses

All experiments were performed in triplicate for at least three individual experiments (N=3). Statistical significance was determined via ANOVA and Dunnett's post hoc analysis to assess differences between individual treatment groups. Significance determined as p-value >0.05. All statistics and graphics will be performed using GraphPad Prism software.

EXAMPLE 1—Effect of Differential APEX Formulation on Exosomal Isolation

Figure 3A:
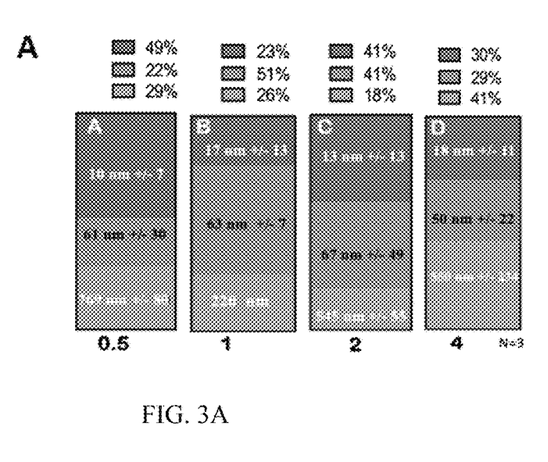
FIGS. 3A-3D show APEX formulation determines EV size and quantity. (3A) Dynamic light scattering reveal different EV subsets sizes. (3B) Increased protamine concentration yields more EV protein. (3C) Exosome measurement via Fluorocet ELIS. (3D) NTA show increased particles with protamine concentration. Statistical significance determined by ANOVA, post hoc analysis Dunnett's *$p>0.5$, *$p>0.001$, and **$p>0.0001$.

The effect of protamine concentration (0.5 mg/mL, 1 mg/mL, 2 mg/mL, and 4 mg/mL) on exosomal yield was evaluated first. The pH was not altered. The APEX to sample ratio was kept at 1:5 and the incubation time was kept at overnight (~16 hrs). DLS was the first test implemented to examine the EV size distribution. The particles were grouped into three categories base on their size range. The exosomal size range was 30-150 nm (green). Any particles over 150 nm were grouped together (red) and could possibly be large EV such as microvesicles or can be aggregated exosomes. Particles under 30 nm were grouped together (blue) and could be aggregated protein or exomeres. Based on the EV size distribution, we observed higher particles in the exosomes size range at protamine concentration of 1 and 2 mg, 51% and 41% respectively (FIG. 3A).

Figure 3B:
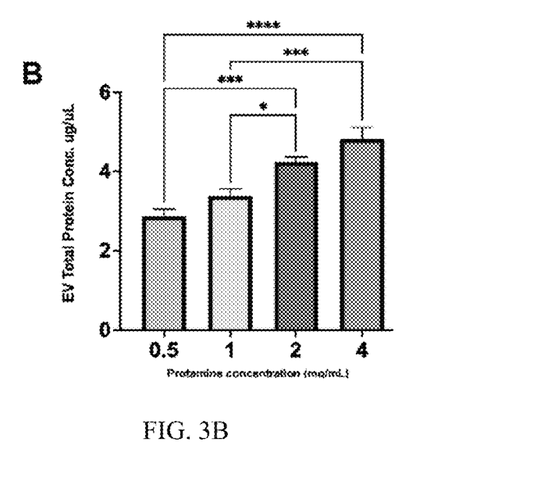
Figure 3C:
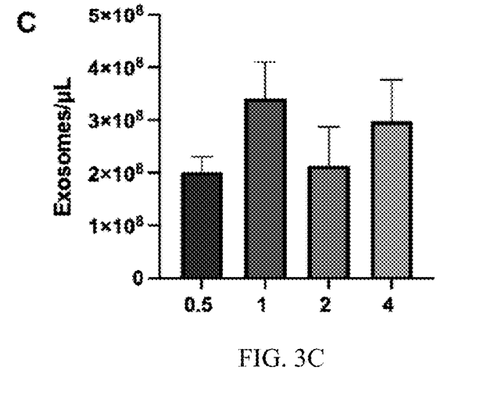
Figure 3D:
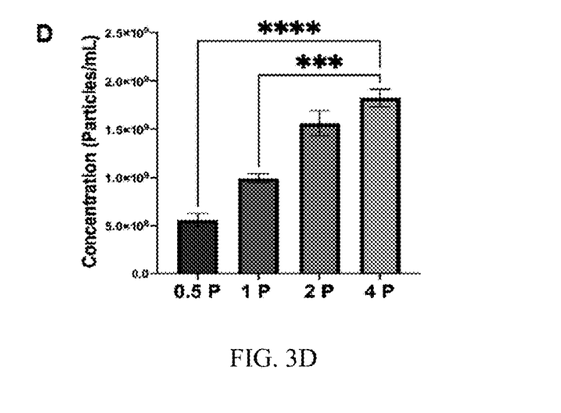

Next, the protein concentration of each protamine concentration samples was quantified via DC protein assay. As the protamine concentration increase, the sample protein concentration increases as well (FIG. 3B). The increase in the sample protein concentration could be because more protamine is being added to the sample. Thus, four approaches (two semi-quantitative and two quantitative) were implemented to quantify the exosomes. Quantitatively, the samples were quantified via Fluorocet and NTA (FIG. 3D). There was no significant difference between the protamine concentration measure by Fluorocet (FIG. 3C). However, higher protamine concentration significantly increased particles concentration when measure via NTA.

Figure 4A:
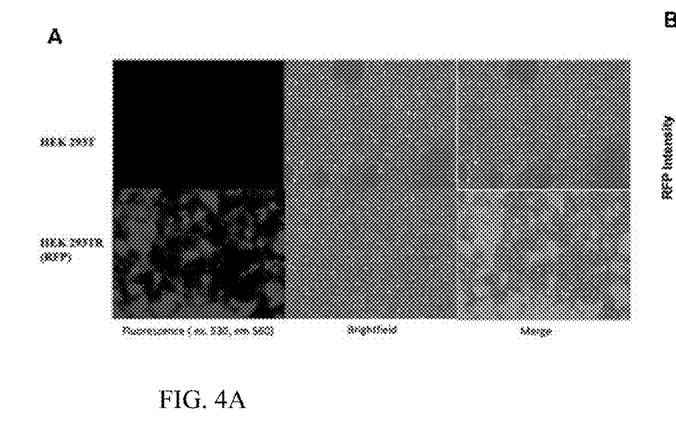
FIGS. 4A-4D show RFP-exosome isolation via APEX formulations. (4A) Tranfected 293t producing RFP-exosomes. (4B) RFP intensity compared on fluorometer. (4C) High protamine concentrations yield more RFP-exosomes. (4D) Western blot confirming presence of exosomal markers CD63 and TSG101 on APEX-isolated RFp exosomes. Statistical significance determined by student T-test, ****$p<0.0001$.
Figure 4B:
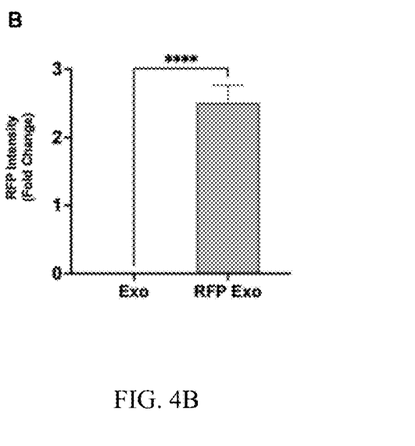
Figure 4C:
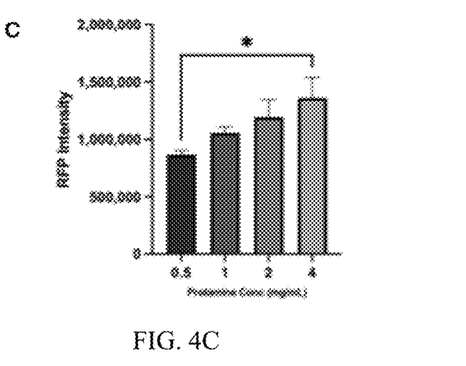
Figure 4D:
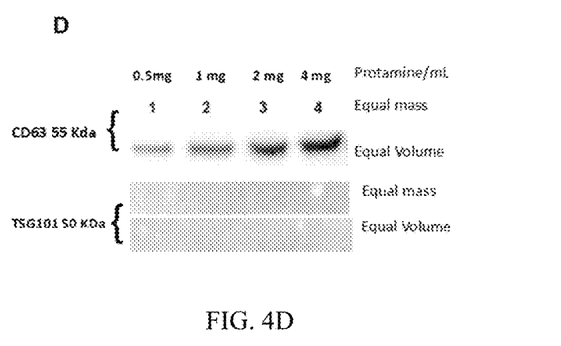
Figure 5A:
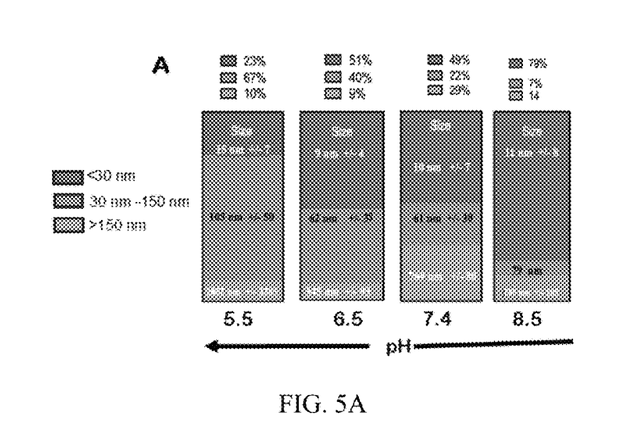
FIGS. 5A-5E show pH modulates exosome yield. (5A) DLS shows APEX isolation of exomere-sized vesicles at pH 8.5 and exosomes at pH-5. (5B) Acidic pH results in more EV proteins. (5C, 5D) Exosome concentration elevated by acidic pH. (5E) Western blot analysis revealed increased exosomal marker and at various acidic pH. Statistical significance determined by ANOVA, and post hic analysis test Dunnett's. *p<0.05, p<0.01. * P<0.0001, and ****p<0.00001.
Figure 5B:
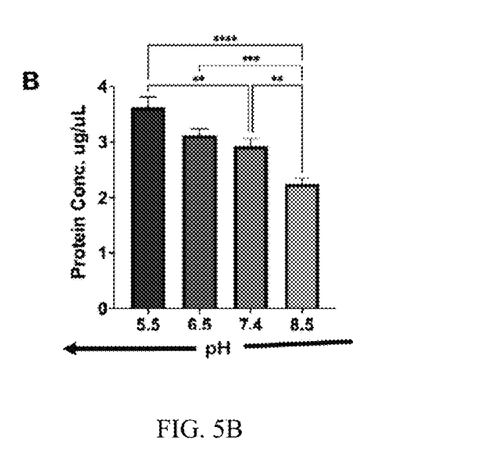

HEK293T cells were transfected with an RFP X-Pack plasmid to express exosomes labelled with RFP (FIG. 4A). Next, the samples exosomes concentrations were assessed semi-quantitatively by measuring the intensity of the RFP exosomes (FIG. 4B). Higher concentration of RFP exosomes should display higher intensity. Higher intensity can be observed as the protamine concentration increase (FIG. 4C). Lastly, a western blot analysis was performed to quantify the exosomes concentration by loading equal volume. Darker bands were observed as the protamine concentration increase (FIG. 4D). Overall, more exosomes are isolated with higher protamine concentration suggesting that positively charged protein polymers facilitate exosomes isolation EXAMPLE 2—Exosomal Isolation and the Effect of pH Based on protein isoelectric point, lowing the pH will increase the amount of positively charged proteins in a solution. For these studies protamine concentration was kept at the lowest (0.5 mg/mL). Next, the pH of the supernatant was changed before adding APEX at a ratio of 1:5 and incubated for overnight. Exosome size increased as the pH was more acidic (FIG. 5A). A total protein assay was performed and higher protein concentrations were observed as the sample becomes more acidic (FIG. 5B).

Figure 5C:
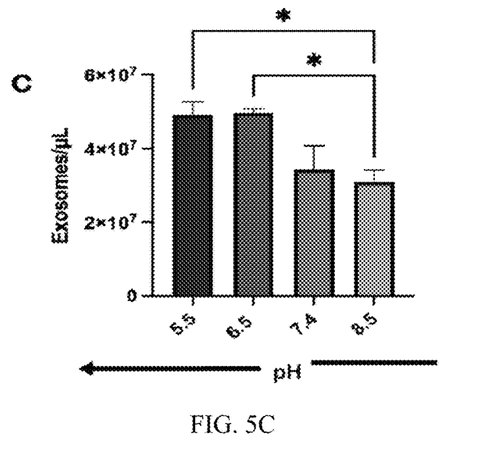
Figure 5D:
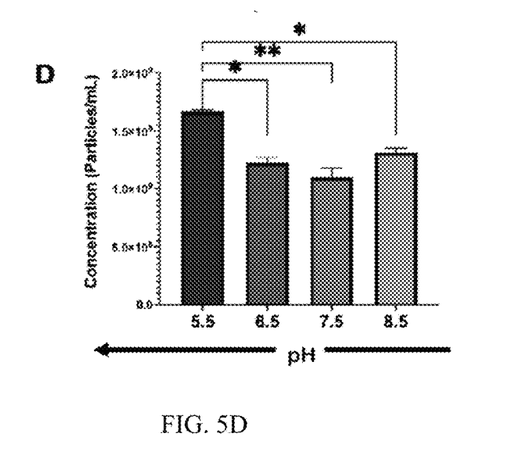
Figure 5E:
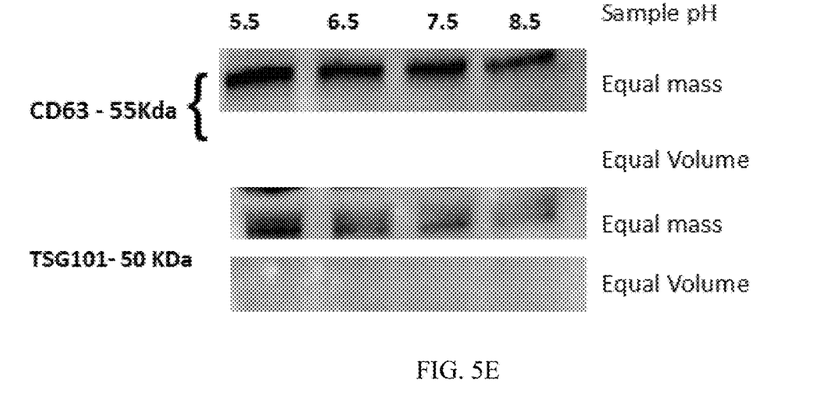

To quantify the exosomes yield, the exosome concentration was determined using a Fluorocet ELISA. Lowering the pH significantly increased the exosomes protein concentration (FIGS. 5B and 5C). The NTA analysis also confirmed higher particles concentration at low pH (FIG. 5C). Next, RFP exosome concentration as previously mentioned, was examined via spectroscopy. RFU values are significantly higher at pH 5.5 (FIG. 5D). Western blot analysis showed darker bands at acidic pH when assessed via a western blot (FIG. 5E). These results suggest that acidic pH increased exosome yield.

EXAMPLE 3—APEX to Sample Ratio on Exosomes Isolation

Figure 6A:
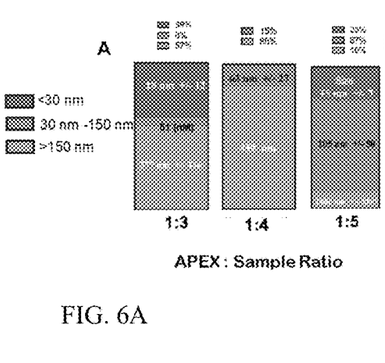
FIGS. 6A-6E show APEX: Sample ration critical to exosome isolation yield and subset. (6A) DLS show 1:5 ratio yielded more exosome-sized vesicles. (6B) EV protein concentration highest at 1:3 ratio. (6C, 6D) Concentration of exosomes highest at 1:3 ratio as measured via DLS and NTA, respectively. (6E) Western blot confirms highest exosome concentration based on exosome markers, CD63 and TSG101 at 1:3 ratio.
Figure 6B:
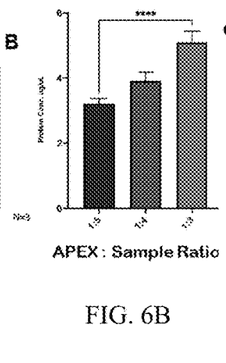
Figure 6C:
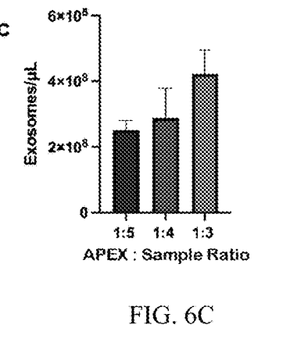
Figures 6D, 6E:
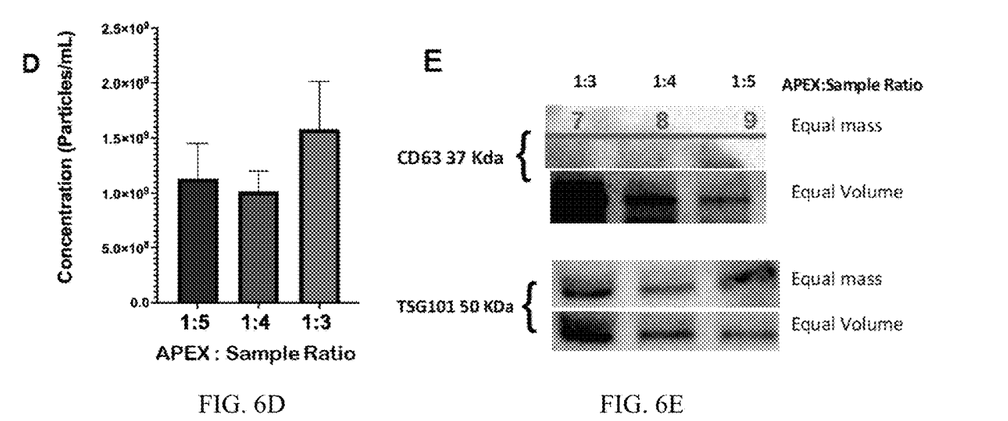

Evaluation of the APEX:sample ratio (1:3, 1:4, and 1:5) was performed next. The samples were kept at the protamine concentration of 0.5 mg/mL. The pH of the sample was adjusted to 5.5 and the samples were finally incubated for overnight. Based on the zetasizer, ratio 1:5 gave the highest exosomal EV size distribution (FIG. 6A). Next, higher protein concentration were observed at the ratio of 1:3 and had the highest concentration of exosomes (FIGS. 6B and 6C). The NTA results also confirmed higher particles concentration at the ratio 1:3 (FIG. 6D). Last, a significantly increase in RFU value was obtain at the 1:3 ratio (FIG. 6E). The 1:3 ratio when assessed via a western blot showed elevated TSG101 and Hsp70. Ultimately, as the ratio of 1/3 had the most exosomes concentration.

EXAMPLE 4—Incubation Time on APEX Isolation

Figure 7A:
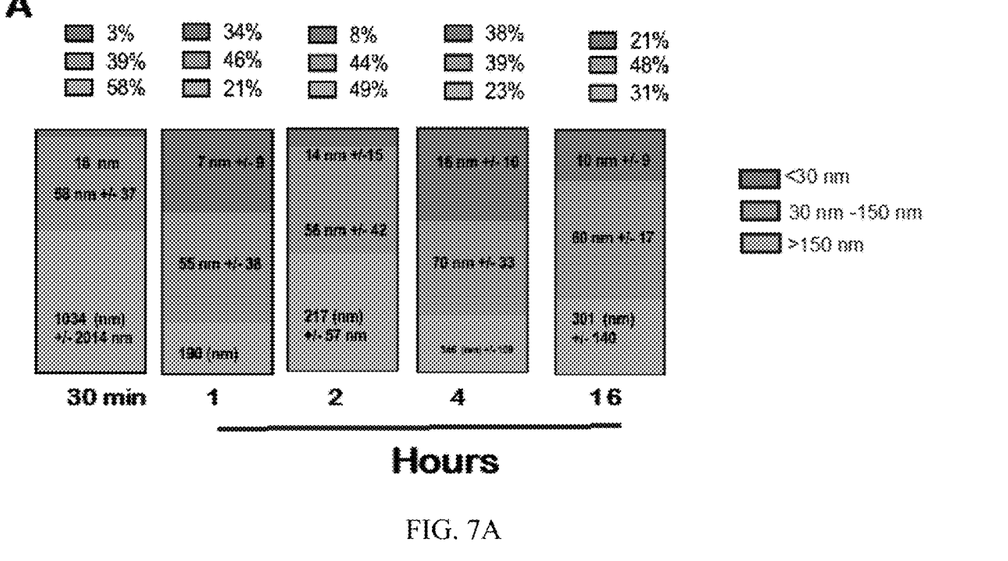
FIGS. 7A-7C show APEX incubation time and exosome yield. (7A) DLS of APEX isolated exosomes derived from tissue culture supernatants incubated with APEX for 1, 2, 4, and 16 hours. (7B) Protein concentration of exosomes lysates as measured by DC protein assay. Protein concentration plateaued at 2 hours. (7C) Exosome concentration determined by ELISA indicated that APEX isolated most of the exosomes within 30 minutes. Red box shows exosomes isolated (*APEX formulation 0.5 P).
Figure 7B:
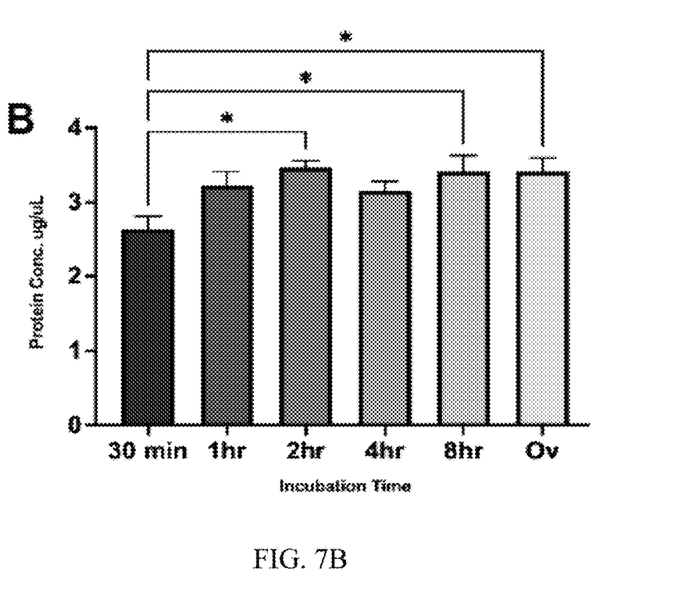
Figure 7C:
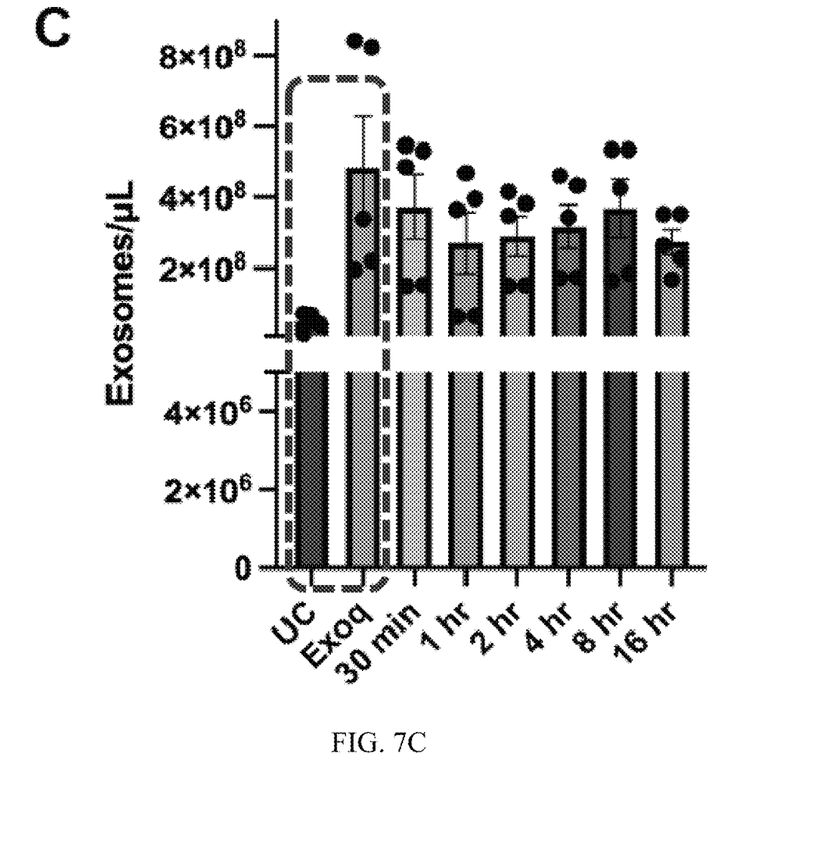

The impact of incubating time of APEX with the sample on exosomal yield was assessed. Based on DLS, the 1-hour incubation yields the highest exosome and exomere-sized vesicles percentage at 80% (FIG. 7A). The 16-hour incubation resulted in 69% exosome/exomere sized vesicles, suggesting that the difference in isolation of exosome subset isolation may occur as within an hour. The highest exosomal protein concentration was observed at the 2-hour incubation (FIG. 7B). The concentration of exosomes quantified via ELISA showed that the exosome yield plateaued at the 30-minute incubation (FIG. 7B). APEX isolation of exosomes compared to the gold standard resulted in 4-fold more exosomes while Exoquick preparation was not significantly different (FIG. 7C).

Taken together, the results showed that the APEX isolated exosome as well as popular commercially available precipitation product and the differential centrifugation gold standard. APEX can be used to isolate the newly discovered EV subsets-exomeres, small, and large exosomes. The pH-dependent APEX methodology allows for inexpensive and rapid isolation of exosomes and exosome subsets. This is the first method that allows for the isolation of all exosomal EV subsets based on pH and charge-based precipitation.

Overall, acidic pH and increasing the APEX to Sample ratio increased the exosome yield when protamine concentration is at 0.5 mg/mL. Parameters that would affect the exosome yield-protamine concentration, pH, incubation time, and APEX:sample ratio were screened.

The APEX concept is based on aggregating the exosomes for precipitate at a lower centrifugation speed. Exosomes' negative zeta potential must be neutralized to prevent them from repelling each other. Exosomes tend to have a net negative zeta potential. Thereby positively charged proteins can interact with exosomes to minimize the overall negative charge that exosomes possess and allow the exosomes to aggregate. Proteins can switch their charge from negative to positive based on their isoelectric point and the pH. Lowering the pH causes more proteins to carry a positive charge. Protamine is a positively charged protein with an isoelectric point between 10-13. Thereby, protamine remains positive in any pH lower than 10. Moreover, at lower pH, more exosomes are isolated because most extracellular proteins in the culture medium carry a positive charge. Ultimately the positively charged proteins help to aggregate and precipitate exosomes. Thus, this method is inexpensive, less laborious, and can be modified for exosome subset-specific isolations, thereby opening the field of EV research.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application and the scope of the appended claims. These examples should not be construed as limiting.

We claim:
1. A method of Absolute Precipitation of Exosomes (APEX) from a sample, the method comprising:
    preclearing the sample to remove cells, dead cells, and/or cell debris;
    mixing the sample with an APEX solution comprising protamine or a salt thereof, and polyethylene glycol (PEG);
    incubating the mixture of the sample and the APEX solution; and
    collecting exosomes from the mixture,
    wherein the method further comprises adjusting the sample to an acidic pH prior to mixing with the APEX solution.
2. The method of claim 1, the sample being a biological fluid, cell culture or culture medium.
3. The method of claim 2, the biological fluid being selected from saliva, serum, urine, blood, plasma, tears, sweat, joint fluid, cerebrospinal fluid, semen, vaginal fluid, ascitic fluid, and amniotic fluid.
4. The method of claim 1, the step of preclearing the sample comprising:
    1) Centrifuging the sample at 300×g for at least ten minutes to remove cells from the sample;
    2) Collecting the supernatant of step 1) and centrifuging the supernatant of step 1) at 3000×g for at least ten minutes to remove dead cells from the sample;
    3) Collecting the supernatant of step 2) and centrifuging the supernatant of step 2) at 20,000×g for 30 minutes to remove cell debris from the sample; and
    4) Collecting the supernatant of step 3).
5. The method of claim 1, the PEG being PEG 32,000.
6. The method of claim 1, the APEX solution being mixed with the sample at a ratio of 1:1, 1:2, 1:3, 1:4, 1:5, 1:6, 1:7, 1:8, 1:9, or 1:10.
7. The method of claim 1, the APEX solution comprising protamine or a salt thereof, and PEG at a ratio (by weight) of 1:2000, 1:1000, 1:500, 1:400, 1:250, 1:200, 1:100, 1:50, or 1:40.
8. The method of claim 1, wherein the mixture is incubated for at least 30 min.
9. The method of claim 1, wherein the collecting exosomes step comprises centrifuging the mixture; collecting the exosome-containing pellet; and resuspending the exosome-containing pellet.
10. The method of claim 9, wherein the mixture is centrifuged at 1500 g for at least 30 min.
11. A method for isolating exosomes from a culture medium, the method comprising:
    providing a cell culture;
    collecting a culture medium of the cell culture;
    preclearing the culture medium to remove cells, dead cells, and/or cell debris by centrifugation;
    collecting a supernatant and adjusting the supernatant to an acidic pH;
    adding, to the supernatant, an APEX solution comprising protamine or a salt thereof, and PEG;
    incubating the mixture of the supernatant and the APEX solution; and
    isolating exosomes from the mixture.
12. The method of claim 11, wherein the preclearing step comprises:
    1) Centrifuging the culture medium at 300×g for at least ten minutes to remove cells;
    2) Collecting the supernatant of step 1) and centrifuging the supernatant of step 1) at 3000×g for at least ten minutes to remove dead cells;

3) Collecting the supernatant of step 2) and centrifuging the supernatant of step 2) at 20,000×g for 30 minutes to remove cell debris; and 4) collecting the supernatant of step 3).

13. The method of claim 11, the acidic pH being from about 4.5 to about 6.5.

14. The method of claim 11, the APEX solution being mixed with the supernatant at a ratio of 1:1, 1:2, 1:3, 1:4, 1:5, 1:6, 1:7, 1:8, 1:9, or 1:10.

15. The method of claim 11, the APEX solution comprising protamine or a salt thereof, and PEG at a ratio (by weight) of 1:2000, 1:1000, 1:500, 1:400, 1:250, 1:200, 1:100, 1:50, or 1:40.

16. The method of claim 11, wherein the mixture is incubated for at least 30 min.

17. The method of claim 11, wherein the isolating exosomes from the mixture comprises centrifuging the mixture at 1500 g for at least 30 min to collect an exosome-containing pellet; and resuspending the pellet in a buffer to arrive at an exosome solution.

* * * * *